Jan. 4, 1938. L. BURBANK Plant Pat. 267
ROSE
Filed Dec. 14. 1936
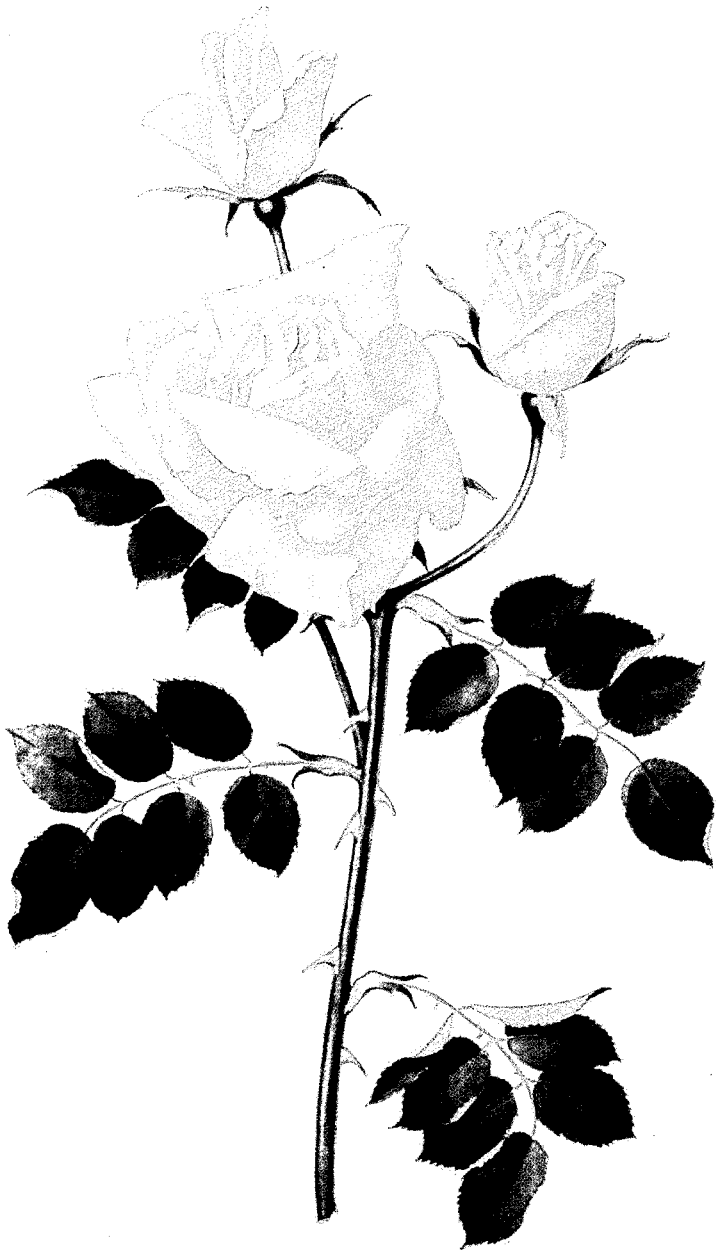
Elizabeth Waters Burbank
Executrix of the estate of
Luther Burbank
By Robbins & Robbins
Attorneys Patented Jan. 4, 1938

Plant Pat. 267

UNITED STATES PATENT OFFICE

267

ROSE

Luther Burbank, deceased, late of Santa Rosa, Calif., by Elizabeth Waters Burbank, executrix, Santa Rosa, Calif., assignor to Stark Bro's. Nurseries & Orchards Company, Louisiana, Mo.

Application December 14, 1936, Serial No. 115,879

1 Claim. (Cl. 47—61)

This invention relates to a new and distinct variety of rose plant of the climbing type, a seedling of unknown parentage, the novel characteristics of which reside in its white color and tea rose type of growth, combined with long seasons of blooming and unusual hardiness.

This climbing rose is notable for its production of a profusion of blooms during the months of May and June.

Its buds are long and pointed, having the same general form as the bud of the bush rose known as Kaiserin Auguste Viktoria, but whereas the bud of this last rose has a creamy-white cast, that of the present climbing rose has a greenish-white cast.

As regards the open flower, the rose of this invention is very double and a lemon-white color, borne on long, strong stems, and when used as cut flowers it has all the appearance of a tea rose in form. The present rose makes an excellent cutting flower because of its long, strong stems and its lasting quality after cutting.

The flower is large, being as large or larger even than that of the Kaiserin Auguste Viktoria and the full blown roses are slightly cupped. The new variety has a strong old rose fragrance.

Referring to the foliage, this plant is characterized as follows:

*Habit of growth.*—Vigorous, thrifty; compact; *Height when full grown.*—From eight to ten feet.

*Hardiness.*—Same as Paul's Scarlet climber.

*Leaflets.*—Seven;

*Size.*—Medium to small; 3½ inches in length. End leaflet is 1¼ inches.

The foliage is abundant, new growth being light green to bronzy on upper side and glossy. Old foliage is medium green to bronzy.

This new variety of rose most closely resembles the well known rose called "Silver Moon", but upon careful examination it is found to differ in the following respects:

| | Silver Moon | New variety |
|---|---|---|
| Bud | Light buff in color | Greenish-white. |
| Flower | Semi-double<br>Little or no fragrance | Very double.<br>Strong old rose.<br>*Petal persistence*—Drop off cleanly. Very disease resistant. Blooms in May and June only. |
| Form | Flat | Slightly cupped. |
| | White in color | Lemon-white. |

The rose hereinbefore set forth has been asexually reproduced through three generations and it has been found that the characteristics are fixed. The tests of this rose were conducted in the Burbank Gardens in California and the Stark gardens at Marionville and Louisiana, Missouri.

Having thus described this rose, what is claimed as new is:

A new and distinct variety of climbing rose plant, characterized by its white tea rose-like flower, borne on long, strong stems, with old rose fragrance, substantially as shown and described.

ELIZABETH WATERS BURBANK,
*Executrix of the Estate of Luther Burbank, Deceased.*